United States Patent
Chen et al.

(10) Patent No.: US 7,662,834 B2
(45) Date of Patent: Feb. 16, 2010

(54) METHODS OF 1H-INDOL-3-YL-2-OXOACETAMIDE COMPOUNDS

(75) Inventors: Chiung-Tong Chen, Taipei (TW); Shu-Jen Chen, Taipei (TW); Ming-Chu Hsu, Taipei (TW); Der-Ren Hwang, Taipei (TW); Wen-Tai Li, Taipei (TW); Chu-Chung Lin, Taipei (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 12/132,254

(22) Filed: Jun. 3, 2008

(65) Prior Publication Data

US 2008/0242701 A1 Oct. 2, 2008

Related U.S. Application Data

(62) Division of application No. 11/145,628, filed on Jun. 6, 2005, now Pat. No. 7,396,838, which is a division of application No. 10/310,711, filed on Dec. 5, 2002, now Pat. No. 6,903,104.

(60) Provisional application No. 60/337,962, filed on Dec. 6, 2001.

(51) Int. Cl.
| | |
|---|---|
| A01N 43/42 | (2006.01) |
| A61K 31/47 | (2006.01) |
| A61K 31/44 | (2006.01) |
| A61K 31/425 | (2006.01) |
| A01N 43/80 | (2006.01) |

(52) U.S. Cl. .................. 514/314; 514/339; 514/372
(58) Field of Classification Search ................ None
See application file for complete search history.

(56) References Cited

U.S. PATENT DOCUMENTS

| | | | |
|---|---|---|---|
| 2,825,734 A | 3/1958 | Speeter | |
| 3,351,630 A | 11/1967 | Shen | |
| 5,192,770 A | 3/1993 | Clark et al. | |
| 6,008,231 A | 12/1999 | Lebaut et al. | |
| 6,114,355 A | 9/2000 | D'Amato | |
| 6,232,327 B1 | 5/2001 | Nickel et al. | |
| 6,251,923 B1 | 6/2001 | Hofgen et al. | |
| 6,469,006 B1 | 10/2002 | Blair et al. | |
| 6,613,794 B2 | 9/2003 | Hofgen et al. | |

FOREIGN PATENT DOCUMENTS

| | | |
|---|---|---|
| DE | 198 18 964 | 11/1999 |
| EP | 0 657 110 A1 | 10/1995 |
| GB | 1028812 | 5/1966 |
| JP | 57006878 | 1/1982 |
| NL | 6502481 | 2/1965 |
| WO | WO 99/51224 | 10/1999 |
| WO | WO 02/08225 A1 | 1/2002 |
| WO | WO 03/022280 A2 | 3/2003 |

OTHER PUBLICATIONS

Dorwald F. A. Side Reactions in Organic Synthesis, 2005, Wiley: VCH, Weinheim p. IX of Preface.*
Draetta, G et. al., Annual Rports in medicinal Chemistry, vol. 31, 1996, p. 241-246.*
Brown, et. al., Oncol Res. 1997, 9(5), p. 213-215.*
Weinstein et. al., Science, 1997, 275(5298), p. 343-349.*
Hamburger et. al., JNCL, 66 (6) 1981, p. 981-986.*
Cecil Textbook of Medicine, 21st Edition (2000), Goldman & Bennett (Editors), W.B. Saunders Company (Publisher), Chapter 198, pp. 1060-1074.*
Internal Medicine, 4th Edition, Editor-in-Chief Jay Stein, Chapters 71-72, pp. 699-715.*
Patterson, A. M. et al., "The Ring Index $2^{nd}$ Ed.", American Chemical Society, Columbus, OH 1960, entry #2527, p. 326.
Draetta, G. et al., Annual Reports in Medicinal Chemistry, vol. 31, 1996, p. 241-246.
Brown, et al., Oncol. Res. 1997 9(5), p. 213-215.
Weinstein et al., Science, 1997, 275(5298), p. 343-349.
Hamburger et al., JNCL, 66(6) 1981, p. 981-986.
In re *Rainer*, 146 USPQ 218 (1965).
In re *Colianni*, 195 USPQ 150, *Ex parte Formal*, 230 USPQ 546.
In re *Fisher*, 427 F.2d 833, 839; 166 USPQ 18, 24 (CCPA 1970).
In re *Wright*, 999 F.2d 1557, 1562; 27 USP@2d 1510, 1513 (Fed. Cir. 1993).

* cited by examiner

*Primary Examiner*—James O Wilson
*Assistant Examiner*—Jeffrey H Murray
(74) *Attorney, Agent, or Firm*—Occhiuti Rohlicek & Tsao LLP

(57) ABSTRACT

This invention relates to treating cancer or an angiogenesis-related disease using a compound of formula 1:

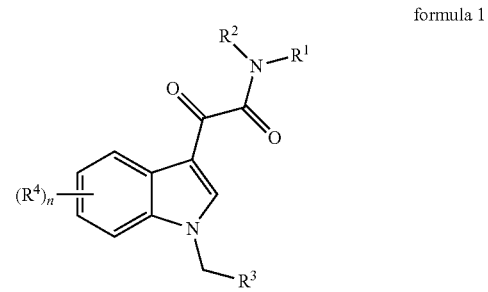

wherein $R^1$, $R^2$, $R^3$, $R^4$, and n are defined herein.

14 Claims, 2 Drawing Sheets

METHODS OF 1H-INDOL-3-YL-2-OXOACETAMIDE COMPOUNDS

RELATED APPLICATIONS

This application is a divisional of U.S. patent application Ser. No. 11/145,628, filed Jun. 6, 2005, now allowed, which is a divisional of U.S. application Ser. No. 10/310,711, filed on Dec. 5, 2002, now U.S. Pat. No. 6,903,104, which claims priority to U.S. Provisional Application No. 60/337,962, filed on Dec. 6, 2001. The contents of all of the prior applications are hereby incorporated by reference in their entireties.

TECHNICAL FIELD

This invention relates to novel heterocyclic compounds and compositions thereof, and their use for the prevention and treatment of disease.

BACKGROUND

Cancer is the leading or second most common cause of death in advanced countries. Despite continuing advances in both diagnosis and treatment, most existing treatment methods have undesirable side effects and limited efficacy in treating and curing the cancerous diseases of solid tumors. Treatment of cancer is complicated by the variety and number of mechanisms involved in the formation and metastasis of tumors, many of which are still not well understood. Chemotherapy is, however, still one of the major options available for the first-line treatment in cancers such as leukemias and second-line treatment for refractory solid tumors. The mechanism of action of some effective anticancer agents remains unclear. Most of the currently used anticancer agents are small molecule chemicals and need to be administered into patients via a parenteral infusion or bolus injection. Clinical complications with the parenteral administrations have been documented and thus extra cares and cost for hospitalization are essential. Recent efforts in the discovery of anticancer drugs have been focused on finding orally active anticancer agents.

Angiogenesis refers to the generation of new blood vessels into a tissue or organ. Under normal physiological conditions, humans or animals only undergo angiogenesis in very specific situations. For example, angiogenesis is normally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to uncontrolled angiogenesis. Thus, methods and compositions are needed to be capable of inhibiting angiogenesis.

The invention presents heterocyclic compounds that exhibit cytotoxic and anticancer activity and that inhibit angiogenesis.

SUMMARY

The invention relates to heterocyclic compounds, compositions including the compounds, and the methods of using the compounds and compound compositions. The compounds and compositions are useful for treating disease or disease symptoms (e.g., cancer). The invention also provides for methods of making the compounds.

The invention is based on the discovery that certain heterocyclic compounds have potent anticancer and cytotoxic activity and inhibit angiogenesis. Thus, this invention relates to novel heterocyclic compounds and to their uses in the medical treatment of disease. The invention is further based on the discovery that certain indol-3-yl oxoacetamido compounds have potent anticancer and cytotoxic activity and are useful in the treatment of a variety of cancers. The invention is further based on the discovery that certain indol-3-yl oxoacetamido compounds have potent anti-angiogenic activity and are useful in the treatment of a variety of angiogenesis-mediated diseases.

In one aspect, the invention relates to a heterocyclic compound of the following formula:

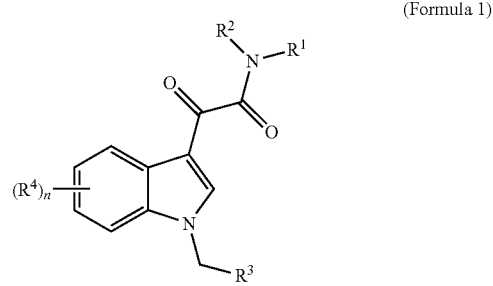

(Formula 1)

wherein, each $R^1$ is independently isoxazolyl, thiazolyl, isothiazolyl, 1,3,4-thiadiazolyl, 1,3-benzothiazolyl, quinolyl, isoquinolyl, thionaphthenyl, or benzofuranyl, each being optionally substituted with 1-6 independent $R^5$; or when taken together with $R^2$ and the nitrogen atom to which they are attached form a 5-8 membered ring comprising C, N, S, or O atoms wherein any atom is optionally substituted with an independent $R^5$;

each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$;

each $R^3$ is independently C1-C10 alkyl, C2-C10 alkenyl, C2-C10 alkynyl, C3-C10 cycloalkyl, C4-C10 cycloalkenyl, aryl, heteroaryl, or heterocyclyl, each being optionally substituted with 1-4 independent $R^5$;

each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O\ R^7$;

each n is 0, 1, 2, 3, or 4;

each $R^5$ is independently H, C1-C10 alkyl optionally substituted with 1-4 independent $R^6$, C2-C10 alkenyl, C2-C10 alkynyl, C3-C10 cycloalkyl, aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2O\ R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$;

each $R^6$ is independently C1-C10 alkyl, C2-C10 alkenyl, C2-C10 alkynyl, halo, haloalkyl, CN, $NO_2$, $OR^7$, or $SO_2R^7$;

each $R^7$ is independently H, $OR^9$, C1-C10 alkyl, C2-C10 alkenyl, C2-C10 alkynyl, C3-C10 cycloalkyl, aryl, heteroaryl, or heterocyclyl, each optionally substituted with 1-4 independent $R^8$;

each $R^8$ is independently H, OH, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$.

In other aspects, the compounds are those of formula 1, described above, wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl. This proviso may only apply to methods of treating cancer or to the compounds themselves.

In other aspects, the compounds are those of formula 1, described above, wherein $R^1$ is isothiazolyl, isoxazolyl, or thiazolyl, each being optionally substituted with 1-4 C1-C10 alkyl; or wherein $R^1$ is 3-methyl-5-isothiazolyl; or wherein each $R^3$ is cyanophenyl, chlorophenyl, 3-methyl-5-isoxazolyl, 3-phenyl-5-isoxazoyl, pyridyl, or thiophenyl; or wherein $R^1$ is 3-methyl-5-isothiazolyl, 3-methyl-5-isoxazolyl, 3-phenyl-5-isoxazolyl, 3-tert-butyl-5-isoxazolyl, 4-methyl-1,3-thiazol-2-yl, or 1,4-benzodioxan-6-yl, thiazolyl, and $R^3$ is cyanophenyl, 3-methyl-5-isoxazolyl, or thiophenyl; or wherein $R^1$ is 3-methyl-5-isothiazolyl, 3-methyl-5-isoxazolyl, or 3-phenyl-5-isoxazolyl, and $R^3$ is cyanophenyl; or pharmaceutically acceptable salt thereof.

In another aspect, the invention is a compound of the following formula:

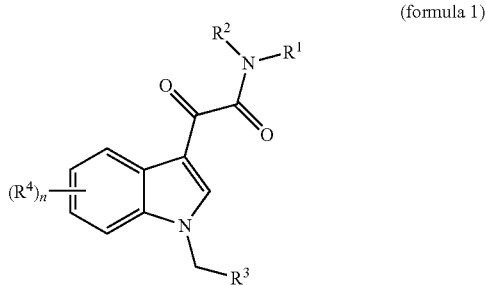

(formula 1)

wherein, each $R^1$ is independently C1-C10 alkyl, C2-C10 alkenyl, C2-C10 alkynyl, C3-C10 cycloakyl, C4-C10 cycloalkenyl, aryl, heteroaryl, or heterocyclyl, each being optionally substituted with 1-6 independent $R^5$; or when taken together with $R^2$ and the nitrogen atom to which they are attached form a 5-8 membered ring comprising C, N, S, or O atoms wherein any atom is optionally substituted with an independent $R^5$;

each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$;

each $R^3$ is independently cyanophenyl, furanyl, thiophenyl, isoxazolyl, thiazolyl, imidazolyl, 4,5-dihydro-5-isoxazolyl, or naphthyl; each being optionally substituted with 1-4 independent $R^5$;

each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O R^7$;

each n is 0, 1, 2, 3, or 4;

each $R^5$ is independently H, C1-C10 alkyl optionally substituted with 1-4 independent $R^6$, C2-C10 alkenyl, C2-C10 alkynyl, C3-C10 cycloalkyl, aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2 OR^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$;

each $R^6$ is independently C1-C10 alkyl, C2-C10 alkenyl, C2-C10 alkynyl, C3-C10 cycloalkyl, halo, haloalkyl, CN, $NO_2$, $OR^7$, or $SO_2R^7$;

each $R^7$ is independently H, C1-C10 alkyl, C2-C10 alkenyl, C2-C10 alkynyl; C3-C10 cycloalkyl; aryl, heteroaryl, or heterocyclyl, each optionally substituted with 1-4 independent $R^8$;

each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$;

wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl.

In other aspects, the invention is a compound of formula 1, wherein each $R^3$ is cyanophenyl, furanyl, or thiophenyl; or wherein each $R^3$ is thiophenyl; or wherein each $R^1$ is 3-methyl-5-isothiazolyl, 1,4-benzodioxan-6-yl or 6-quinolyl; or wherein each $R^1$ is 3-methyl-5-isothiazolyl, pyridyl, halophenyl, or methoxyphenyl, and $R^3$ is 3-alkyl-5-isoxazolyl, 3-aryl-5-isoxazolyl, or cyanophenyl; or wherein each $R^1$ is 3-methyl-5-isothiazolyl or 6-quinolyl, and $R^3$ is furanyl, thiophenyl, or 1-methyl-1H-5-imidazolyl.

In another aspect, the invention is a formulation including a compound of any of the formulae herein, and an excipient suitable for administration to a subject. In another aspect, the invention is a composition including a compound of any of the formulae herein, and a pharmaceutically acceptable carrier.

Additionally, the invention relates to a composition including a compound of any of the formulae herein, a pharmaceutically acceptable carrier, and an additional therapeutic agent.

The additional therapeutic agent can be an anticancer agent. The additional therapeutic agent can also be paclitaxel, docitaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, cytarabine, dactinomycin, interferon alpha, streptozocin, prednisolone, or procarbazine.

In another aspect, the invention is a method of treating a subject (e.g., human, mammal, dog, cat, horse) having cancer including administering to the subject an effective amount of a compound of any of the formulae herein.

The cancer can be a human leukemia, sarcoma, osteosarcoma, lymphoma, melanoma, ovarian, skin, testicular, gastric, pancreatic, renal, breast, prostate colorectal, head and neck, brain, esophageal, bladder, adrenal cortical, lung, bronchus, endometrial, cervical or hepatic cancer, or cancer of unknown primary site. The cancer can also be a cancer of a drug resistance phenotype of which the cancer cells express P-glycoprotein (MDR), multidrug resistance-associated proteins (MRP), lung cancer resistance-associated proteins (LRP), breast cancer resistance proteins (BCRP) or other proteins associated with resistance to anticancer drugs.

In another aspect, the invention is a method of inhibiting angiogenesis in a subject identified as in need thereof, including administering to the subject an effective amount of a compound of any of the formulae herein.

In still another aspect, the invention is a method of treating disease or disease symptoms in a subject, including administration to the subject an effective amount of a compound of any formulae herein. The disease can be angiogenesis-mediated, associated with corneal neovascularization, inflammatory, or any of those specifically recited herein.

Angiogenesis-mediated diseases include choroidal neovascular diseases, retina neovascular diseases, neovascularization of the angle, Bartonellosis, chronic inflammation, osteoarthritis, atherosclerosis phemphigoid, trachoma, or Osler-Webber-Rendu disease.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scieritis, Steven's Johnson disease, periphigoid radial keratotomy, and corneal graph rejection. Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Another disease which can be treated according to the present invention is rheumatoid arthritis. While not being held to any one particular theory, it is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity Other diseases that can be treated according to the present invention are hemangiomas, Osler-Weber-Rendu disease, or hereditary hemorrhagic telangiectasia, solid or blood borne tumors and acquired immune deficiency syndrome.

The methods described herein can further include identifying the subject as in need of a particular treatment. Identifying a subject in need of such treatment can be in the judgement of a subject or a health care professional and can be subjective (e.g., opinion) or objective (e.g., measurable by a test or diagnostic method).

In one aspect, the invention is a compound of any of the formulae herein, wherein each $R^3$ is independently C1-C10 alkyl, C2-C10 alkenyl, C2-C10 alkynyl, C3-C10 cycloalkyl, C4-C10 cycloalkenyl, heteroaryl, or heterocyclyl, each being optionally substituted with 1-4 independent $R^5$.

In another aspect, the invention is a compound of any of the formulae herein, wherein each $R^3$ is independently aryl optionally substituted with 1-4 independent $R^5$.

Another aspect of the invention is a compound of any of the formulae herein, wherein each $R^3$ is independently C1-C10 alkyl, C2-C10 alkenyl, C2-C10 alkynyl, C3-C10 cycloalkyl, C4-C10 cycloalkenyl, aryl, heteroaryl, or heterocyclyl, each being optionally substituted with 1-4 independent $R^5$; wherein $R^3$ is not fluorophenyl.

This invention relates to methods of making compounds of any formulae herein comprising reacting any one or more of the compounds or formulae delineated herein including any processes delineated herein.

The invention further relates to a method of making a compound of formula 1 described above. The method includes taking an indole derivative of the formula:

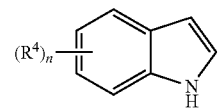

wherein each $R^4$ and n is independently defined herein, included in formula 1; and reacting it with one or more chemical reagents in one or more steps to produce a compound of any of the formulae herein.

The invention also related to a method of making a compound of formula 1 described above, including taking an indole derivative of the formula:

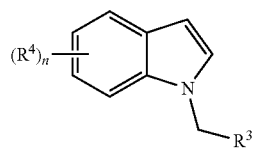

wherein each $R^4$, and n is independently defined herein, including in formula 1; and each $R^3$ is independently C1-C10 alkyl, C2-C10 alkenyl, C2-C10 alkynyl, C3-C10 cycloalkyl, C4-C10 cycloalkenyl, aryl, heteroaryl, or heterocyclyl, each being optionally substituted with 1-4 independent $R^5$; wherein each $R^5$ is independently defined herein, including in formula 1; and reacting it with one or more chemical reagents in one or more steps to produce a compound of any of the formulae herein.

The invention further relates to a method of making a compound of formula 1 described above, including taking an indole derivative of the formula:

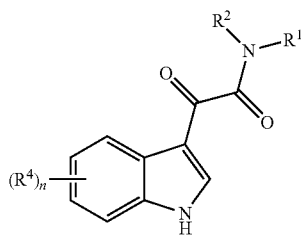

Wherein each $R^4$, and n is independently defined herein, including in formula 1; each $R^1$ is independently C1-C10 alkyl, C2-C10 alkenyl, C2-C10 alkynyl, C3-C10 cycloakyl, C4-C10 cycloalkenyl, aryl, heteroaryl, or heterocyclyl, each being optionally substituted with 1-4 independent $R^5$; wherein each $R^5$ is independently defined as herein, including formula 1, or when taken together with $R^2$ and the nitrogen atom to which they are attached form a 5-8 membered ring comprising C, N, S, or O atoms wherein any atom is optionally substituted with an independent $R^5$; each $R^2$ is independently H, C1-C10 alkyl, or aryl, each being optionally substituted with 1-4 independent $R^5$ or when taken together with $R^1$ and the nitrogen atom to which they are attached form a 5-8 membered ring comprising C, N, S, or O atoms wherein any atom is optionally substituted with an independent $R^5$; wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl; and reacting it with one or more chemical reagents in one or more steps to produce a compound of any of the formulae herein.

The invention also includes a method of making a compound of formula 1:

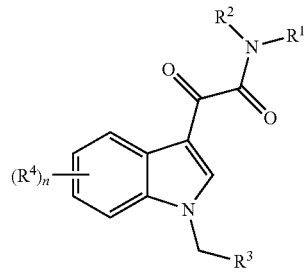

formula 1 wherein each $R^1$ is independently isoxazolyl, thiazolyl, isothiazolyl, 1,3,4-thiadiazolyl, 1,3-benzothiazolyl, quinolyl, isoquinolyl, thionaphthenyl, or benzofuranyl, each being optionally substituted with 1-6 independent $R^5$; or when taken together with $R^2$ and the nitrogen atom to which they are attached form a 5-8 membered ring comprising C, N, S, or O atoms wherein any atom is optionally substituted with an independent $R^5$; each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$; each $R^3$ is independently C1-C10 alkyl, C2-C10 alkenyl, C2-C10 alkynyl, C3-C10 cycloalkyl, C4-C10 cycloalkenyl, aryl, heteroaryl, or heterocyclyl, each being optionally substituted with 1-4 independent $R^5$; each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O\ R^7$; each n is 0, 1, 2, 3, or 4; each $R^5$ is independently H, C1-C10 alkyl optionally substituted with 1-4 independent $R^6$, C2-C10 alkenyl, C2-C10 alkynyl, C3-C10 cycloalkyl, aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, COO $R^7$, $NO_2$, CN, $C(O)R^7$, $C(O)NR^7R^7$, $OC(O)R^7$, $S(O)_2R^7$, $S(O)_2OR^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$; each $R^6$ is independently C1-C10 alkyl, C2-C10 alkenyl, C2-C10 alkynyl, halo, haloalkyl, CN, $NO_2$, $OR^7$, or $SO_2R^7$; each $R^7$ is independently H, C1-C10 alkyl, C2-C10 alkenyl, C2-C10 alkynyl; C3-C10 cycloalkyl; aryl, heteroaryl, or heterocyclyl, each optionally substituted with 1-4 independent $R^8$; each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$; wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl;

by reacting with an indole of formula 2:

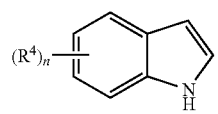

formula 2 wherein $R^4$ and n are each independently as defined above;
with a reagent of formula 3:

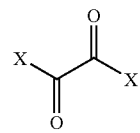

formula 3 wherein X is independently a leaving group;
followed by addition of $HNR^1R^2$, where $R^1$ and $R^2$ are independently as defined above; and reacting the resulting compound of formula 4:

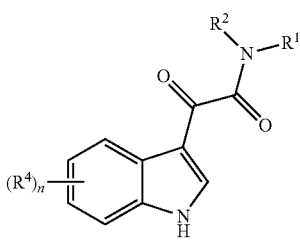

formula 4 wherein all variables are as defined above;

with a base and a compound of the formula $XCH_2R^3$; wherein X is independently a leaving group and $R^3$ is as defined above; resulting in a compound of formula 1.

In certain embodiments, X is independently halo, O-triflate, or alkoxyl.

The invention also relates to a method of making a compound of formula 1:

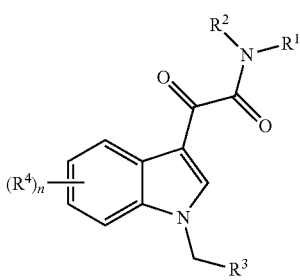

formula 1 wherein each $R^1$ is independently C1-C10 alkyl, C2-C10 alkenyl, C2-C10 alkynyl, C3-C10 cycloakyl, C4-C10 cycloalkenyl, aryl, heteroaryl, or heterocyclyl, each being optionally substituted with 1-4 independent $R^5$; or when taken together with $R^2$ and the nitrogen atom to which they are attached form a 5-8 membered ring comprising C, N, S, or O atoms wherein any atom is optionally substituted with an independent $R^5$; each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$; each $R^3$ is independently cyanophenyl, furanyl, thiophenyl, isoxazolyl, thiazolyl, imidazolyl, 4,5-dihydro-5-isoxazolyl, or naphthyl; each being optionally substituted with 1-4 independent $R^5$; each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O R^7$; each n is 0, 1, 2, 3, or 4; each $R^5$ is independently H, C1-C10 alkyl optionally substituted with 1-4 independent $R^6$, C2-C10 alkenyl, C2-C10 alkynyl; C3-C10 cycloalkyl; aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2OR^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$; each $R^6$ is independently C1-C10 alkyl, C2-C10 alkenyl, C2-C10 alkynyl, halo, haloalkyl, CN, $NO_2$, $OR^7$, or $SO_2R^7$; each $R^7$ is independently H, C1-C10 alkyl, C2-C10 alkenyl, C2-C10 alkynyl; C3-C10 cycloalkyl; aryl, heteroaryl, or heterocyclyl, each optionally substituted with 1-4 independent $R^8$; each $R^8$ is independently H, OH, $OR^9$, C1-C10 alkyl, halo, aryl, $NO_2$; and each $R^9$ is independently H, C1-C10 alkyl, or aryl; each being optionally substituted with 1-4 independent OH, halo, CN, $NO_2$, or $CO_2H$; wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl;

by reacting an indole of formula 2:

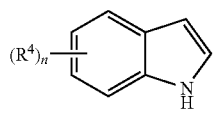

formula 2 wherein each $R^4$ and n is independently as defined above;

with a reagent of formula 3:

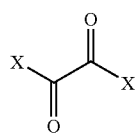

formula 3 wherein X is a leaving group;

followed by addition of $HNR^1R^2$, where $R^1$ and $R^2$ are as defined above; and reacting the resulting compound of formula 4:

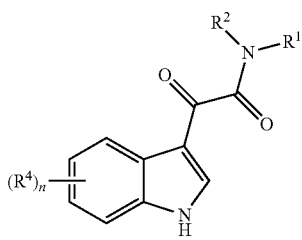

formula 4 wherein all variables are as defined above;

with a base and a compound of the formula $XCH_2R^3$; where X is independently a leaving group and $R^3$ is as defined above; resulting in a compound of formula 1.

The invention also relates to a method of making a compound of formula 1:

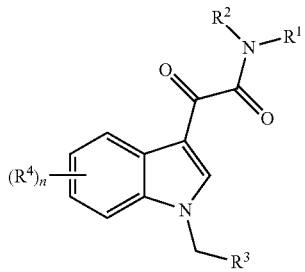

formula 1

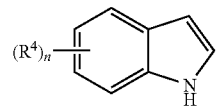

formula 2 wherein each $R^4$ and n is independently defined as above;
with a base, and a compound of the formula $XCH_2R^3$, wherein X is independently a leaving group and $R^3$ is as defined above; and
reacting the resulting compound of formula 3:

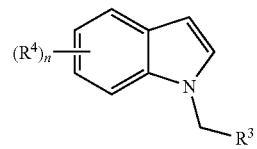

formula 3 where $R^3$, $R^4$ and n are as defined above;
with a reagent of formula 4:

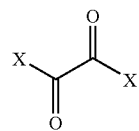

formula 4 wherein X is independently a leaving group;
and a reagent $HNR^1R^2$; where $R^1$ and $R^2$ are as defined above; resulting in a compound of formula 1.

Another aspect of the invention includes a method of making a compound of formula 1

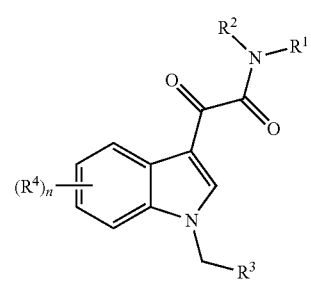

formula 1 wherein each $R^1$ is independently isoxazolyl, thiazolyl, isothiazolyl, 1,3,4-thiadiazolyl, 1,3-benzothiazolyl, quinolyl, isoquinolyl, thionaphthenyl, or, benzofuranyl, each being optionally substituted with 1-6 independent $R^5$; or when taken together with $R^2$ and the nitrogen atom to which they are attached form a 5-8 membered ring comprising C, N, S, or O atoms wherein any atom is optionally substituted with an independent $R^5$; each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$; each $R^3$ is independently C1-C10 alkyl, C2-C10 alkenyl, C2-C10 alkynyl, C3-C10 cycloalkyl, C4-C10 cycloalkenyl, aryl, heteroaryl, or heterocyclyl, each being optionally substituted with 1-4 independent $R^5$; each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O R^7$; each n is 0, 1, 2, 3, or 4; each $R^5$ is independently H, C1-C10 alkyl optionally substituted with 1-4 independent $R^6$, C2-C10 alkenyl, C2-C10 alkynyl; C3-C10 cycloalkyl; aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, $COO R^7$, $NO_2$, CN, $C(O)R^7$, $C(O)NR^7R^7$, $OC(O)R^7$, $S(O)_2R^7$, $S(O)_2OR^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$; each $R^6$ is independently C1-C10 alkyl, C2-C10 alkenyl, C2-C10 alkynyl, halo, haloalkyl, CN, $NO_2$, $OR^7$, or $SO_2R^7$; each $R^7$ is independently H, C1-C10 alkyl, C2-C10 alkenyl, C2-C10 alkynyl; C3-C10 cycloalkyl; aryl, heteroaryl, or heterocyclyl, each optionally substituted with 1-4 independent $R^8$; each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$; wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitro-phenyl)-piperazin-1-yl, 4-(3,5-dimethoxy-phenyl)-piperazin-1-yl, or 4-[bis-(4-fluoro-phenyl)-methyl]-piperazin-1-yl;

including reacting an indole of formula 2:

wherein each $R^1$ is independently C1-C10 alkyl, C2-C10 alkenyl, C2-C10 alkynyl, C3-C10 cycloakyl, C4-C10 cycloalkenyl, aryl, heteroaryl, or heterocyclyl, each being optionally substituted with 1-4 independent $R^5$; or when taken together with $R^2$ and the nitrogen atom to which they are attached form a 5-8 membered ring comprising C, N, S, or O atoms wherein any atom is optionally substituted with an independent $R^5$; each $R^2$ is independently H, C1-C10 alkyl, or aryl, each being optionally substituted with 1-4 independent $R^5$; or when taken together with $R^1$ and the nitrogen atom to which they are attached form a 5-8 membered ring comprising C, N, S, or O atoms wherein any atom is optionally substituted with an independent $R^5$; each $R^3$ is independently cyanophenyl, furanyl, thiophenyl, isoxazolyl, thiazolyl, imidazolyl, 4,5-dihydro-5-isoxazolyl, or naphthyl; each being optionally substituted with 1-4 independent $R^5$; each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2OR^7$; each n is 0, 1, 2, 3, or 4; each $R^5$ is independently H, C1-C10 alkyl optionally substituted with 1-4 independent $R^6$, C2-C10 alkenyl, C2-C10 alkynyl; C3-C10 cycloalkyl; aryl optionally substituted with 1-4 independent $R^6$, heteroaryl optionally substituted with 1-4 independent $R^6$, heterocyclyl optionally substituted with 1-4 independent $R^6$, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2OR^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$; each $R^6$ is independently C1-C10 alkyl, C2-C10 alkenyl, C2-C10 alkynyl, halo, haloalkyl, CN, $NO_2$, $OR^7$ or $SO_2R^7$; each $R^7$ is independently H, C1-C10 alkyl, C2-C10 alkenyl, C2-C10 alkynyl; C3-C10 cycloalkyl; aryl, heteroaryl, or heterocyclyl, each optionally substituted with 1-4 independent $R^8$; each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$; wherein $R^1$ taken together with $R^2$ and the nitrogen atom to which they are attached is not 4-phenyl-piperazin-1-yl, 4-(pyridin-4-yl)-piperazin-1-yl, 4-(pyridin-2-yl)-piperazin-1-yl, 4-(2-nitrophenyl)-piperazin-1-yl, 4-(3,5-dimethoxy-phenyl)-piperazin-1-yl, or 4-[bis-(4-fluoro-phenyl)-methyl]-piperazin-1-yl;

including reacting an indole of formula 2:

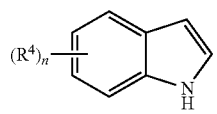

formula 2 wherein each $R^4$ and n is independently as defined above;

with a base, and a compound of the formula $XCH_2R^3$, wherein X is independently a leaving group and $R^3$ is as defined above;

reacting the resulting compound of formula 3:

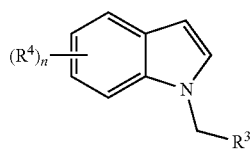

formula 3 where $R^3$, $R^4$ and n are independently as defined above;

with a reagent having formula 4:

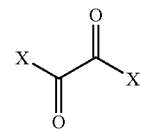

formula 4 wherein X is independently a leaving group; and
a reagent $HNR^1R^2$; where $R^1$ and $R^2$ are as defined above; resulting in a compound of formula 1.

The invention also relates to a method of making a composition including combining a compound of any of the formulae herein with a pharmaceutically acceptable carrier.

Additionally, another aspect of the invention is a method of reducing tumor size including administering a compound of any of the formulae herein.

Thus, one aspect of the invention relates to a method of making a compound of the formulae described herein, including synthesizing any one or more intermediates illustrated in the synthetic schemes herein and then converting that intermediate(s) to a compound of the formulae described herein. Another embodiment relates to a method of making a compound of the formulae described herein, including synthesizing any one or more intermediates illustrated in the examples herein and then converting that intermediate(s) to a compound of the formulae described herein. Another embodiment relates to a method of making a compound of the formulae described herein, including synthesizing any one or more intermediates illustrated in the synthetic schemes herein and then converting that intermediate(s) to a compound of the formulae described herein utilizing one or more of the chemical reactions described in the synthetic schemes or examples herein.

The terms "halo" and "halogen" refer to any radical of fluorine, chlorine, bromine or iodine. The terms "alkyl", "alkenyl" and "alkynyl" refer to hydrocarbon chains that can be straight-chain or branched-chain, containing the indicated number of carbon atoms. For example, C1-C10 indicates the group can have from 1 to 10 (inclusive) carbon atoms in it. The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to a 6-carbon monocyclic or 10-carbon bicyclic aromatic ring system wherein 0, 1, 2 or 3 atoms of each ring can be substituted by a substituent. Examples of aryl groups include phenyl, naphthyl and the like.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heterocyclyl groups include piperazinyl, pyrrolidinyl, dioxanyl, morpholinyl, tetrahydrofuranyl, and the like.

The term "multidrug resistant phenotype" refers to cancer cells that express P-glycoprotein (MDR), multidrug resistance-associated proteins (MRP), lung cancer resistance-associated proteins (LRP), breast cancer resistance proteins (BCRP) or other proteins associated with the resistance to anticancer drugs.

The term "treating" or "treated" refers to administering a compound described herein to a subject with the purpose to cure, heal, alleviate, relieve, alter, remedy, ameliorate, improve, or affect a disease, the symptoms of the disease or the predisposition toward the disease.

"An effective amount" refers to an amount of a compound which confers a therapeutic effect on the treated subject. The therapeutic effect may be objective (i.e., measurable by some test or marker) or subjective (i.e., subject gives an indication of or feels and effect). An effective amount of the compound described above may range from about 0.1 mg/Kg to about 500 mg/Kg, alternatively from about 1 to about 50 mg/Kg. Effective doses will also vary depending on route of administration, as well as the possibility of co-usage with other agents.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject for the treatment of cancer).

Although methods and materials similar or equivalent to those described herein can be used in the practice or testing of the present invention, suitable methods and materials are described below. In addition, the materials, methods, and examples are illustrative only and not intended to be limiting.

The invention can provide several advantages over the existing methods of treatment. For example, the compounds of the invention can have several chemical and pharmacological advantages useful in treating cancer and inhibiting angiogenesis. These advantages can include both chemical stability and pharmacological stability, as well as potency, different resistance profiles, different selectivity profiles, and decreased side-effects. The methods and compositions are orally active against cancer and are capable of inhibiting angiogenesis. A simple and efficacious method of treatment for the invention can be provided by easy administrations through the oral route, which could be distributed in a form that the patient could self-administer repeatedly for multiple doses by which an angiogenesis inhibitor is preferentially administered, sometimes for a long-term regimen for the purpose of disease prevention. The invention also envisions veterinary uses for the treatment of cancer and inhibition of angiogenesis in animals (e.g., dogs, cats, or horses). Thus, a subject as described herein includes these animals as well as humans.

Other features and advantages of the invention will be apparent from the following detailed description, and from the claims.

DETAILED DESCRIPTION

Figure 1:
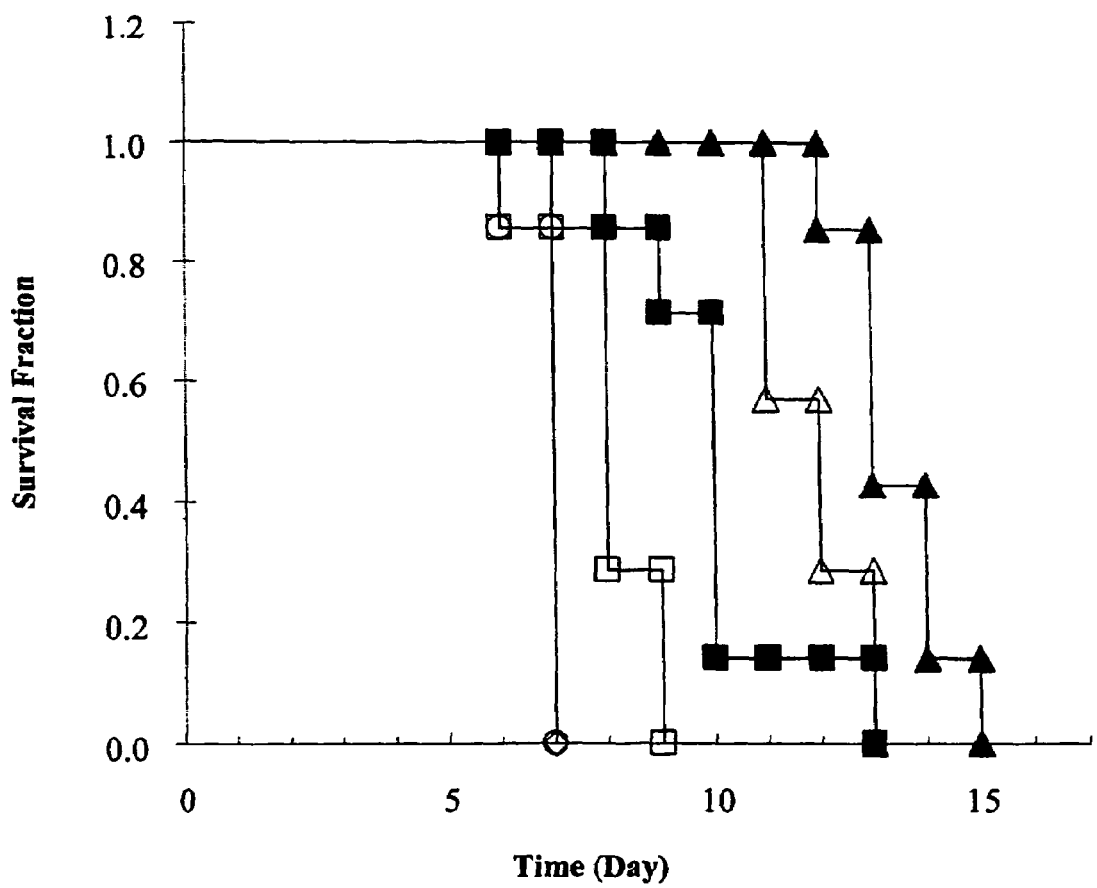
FIG. 1 is a graph of the dose-response relationship of compound 56, showing survival fractions mice.

The invention also relates to the specific compounds exemplified herein. Thus one embodiment of the invention is any compound specifically described herein, including the compounds listed below:

TABLE 1

Compounds

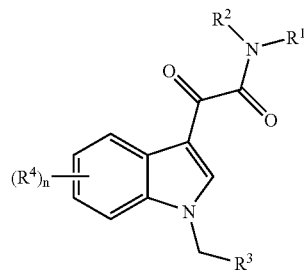

| Compound | $R^1$ | $R^2$ | $R^3$ | $R^4$ |
|---|---|---|---|---|
| 1 | 4-pyridyl | H | 4-cyanophenyl | H |
| 2 | 5-(tert-butyl)-3-isoxazolyl | H | 4-cyanophenyl | H |
| 3 | 6-quinolyl | H | 4-cyanophenyl | H |
| 4 | 4-morpholinophenyl | H | 4-cyanophenyl | H |
| 5 | 2,6-difluorophenyl | H | 4-cyanophenyl | H |
| 6 | 2,6-dichlorophenyl | H | 4-cyanophenyl | H |
| 7 | 4-methoxyphenyl | H | 4-cyanophenyl | H |
| 8 | 1,4-benzodioxan-6-yl | H | 4-cyanophenyl | H |
| 9 | 3-(benzyloxy)phenyl | H | 4-cyanophenyl | H |
| 10 | 3,4,5-trimethoxyphenyl | H | 4-cyanophenyl | H |
| 11 | 4-bromophenyl | H | 4-cyanophenyl | H |
| 12 | 5-methyl-1,3-thiazol-2-yl | H | 4-cyanophenyl | H |
| 13 | 4-iodophenyl | H | 4-cyanophenyl | H |
| 14 | 3,5-dimethyiphenyl | H | 4-cyanophenyl | H |

TABLE 1-continued

Compounds

| Compound | R¹ | R² | R³ | R⁴ |
|---|---|---|---|---|
| 15 | 4-carboethoxyphenyl | H | 4-cyanophenyl | H |
| 16 | benzyl | H | 4-cyanophenyl | H |
| 17 | 4-nitrobenzyl | H | 4-cyanophenyl | H |
| 18 | 1,2,4,5-tetrahydrooxepin-1-yl | H | 4-cyanophenyl | H |
| 19 | 5-bromo-2-pyridyl | H | 4-cyanophenyl | H |
| 20 | 4-(benzyloxy)phenyl | H | 4-cyanophenyl | H |
| 21 | 6-(4-chlorophenyl)hexyl | H | 4-cyanophenyl | H |
| 22 | 4-(dimethylamino)phenyl | H | 4-cyanophenyl | H |
| 23 | 4-(acetylamino)phenyl | H | 4-cyanophenyl | H |
| 24 | 3-methyl-5-isothiazolyl | H | 4-cyanophenyl | 5-Br |
| 25 | 3-methyl-5-isothiazolyl | H | 4-cyanophenyl | H |
| 26 | 5-methyl-1,3,4-thiadiazol-2-yl | H | 4-cyanophenyl | H |
| 27 | 3-methyl-5-isoxazolyl | H | 4-cyanophenyl | H |
| 28 | 3-(tert-butyl)-5-isoxazolyl | H | 4-cyanophenyl | H |
| 29 | 3-phenyl-5-isoxazolyl | H | 4-cyanophenyl | H |
| 30 | 3-(4-chlorophenyl)-5-isoxazolyl | H | 4-cyanophenyl | H |
| 31 | 4-methoxyphenyl | 4-cyanobenzyl | 4-cyanophenyl | H |
| 32 | 4-methoxyphenyl | H | 2-cyanophenyl | H |
| 33 | 4-methoxyphenyl | 2-cyanobenzyl | 2-cyanophenyl | H |
| 34 | 4-methyl-1,3-thiazol-2-yl | H | 4-chlorophenyl | H |
| 35 | 5-methyl-1,3,4-thiadiazol-2-yl | H | 4-chlorophenyl | H |
| 36 | 3-(tert-butyl)-5-isoxazolyl | H | 4-chlorophenyl | H |
| 37 | 3-phenyl-5-isoxazolyl | H | 4-chlorophenyl | H |
| 38 | 3-(4-chlorophenyl)-5-isoxazolyl | H | 4-chlorophenyl | H |
| 39 | 3-methyl-5-isothiazolyl | H | 3,4,5-trimethoxyphenyl | H |
| 40 | 3-methyl-5-isothiazolyl | H | 2-furyl | H |
| 41 | 4-pyridyl | H | 2-furyl | H |
| 42 | 6-quinolyl | H | 2-furyl | H |
| 43 | 6-(4-chlorophenoxy)hexyl | H | 4-cyanophenyl | H |
| 44 | 3-methyl-5-isothiazolyl | H | 2-thienyl | H |
| 45 | 3-methyl-5-isothiazolyl | H | 3-thienyl | H |
| 46 | 3-methyl-5-isoxazolyl | H | 3-thienyl | H |
| 47 | 4-pyridyl | H | 3-thienyl | H |
| 48 | 6-quinolyl | H | 3-thienyl | H |
| 49 | 4-methyl-thiazol-2-yl | H | 3-thienyl | H |
| 50 | 4-methoxyphenyl | H | 3-thienyl | H |
| 51 | 3-methyl-5-isothiazolyl | H | 3-methyl-4,5-dihydro-5-isoxazolyl | H |
| 52 | 3-(4-chlorophenyl)-5-isoxazolyl | H | 3-methyl-4,5-dihydro-5-isoxazolyl | H |
| 53 | 4-bromophenyl | H | 5-isoxazolyl | H |
| 54 | 3-methyl-5-isothiazolyl | H | 5-isoxazolyl | H |
| 55 | 4-pyridyl | H | 5-isoxazolyl | H |
| 56 | 3-methyl-5-isothiazolyl | H | 3-methyl-5-isoxazolyl | H |
| 57 | 3-methyl-5-isoxazolyl | H | 3-methyl-5-isoxazolyl | H |
| 58 | 4-pyridyl | H | 3-methyl-5-isoxazolyl | H |
| 59 | 6-quinolyl | H | 3-methyl-5-isoxazolyl | H |
| 60 | 4-methyl-1,3-thiazol-2-yl | H | 3-methyl-5-isoxazolyl | H |
| 61 | 1,3-benzothiazol-2-yl | H | 3-methyl-5-isoxazolyl | H |
| 62 | 4-bromophenyl | H | 3-methyl-5-isoxazolyl | H |
| 63 | 3-methyl-5-isothiazolyl | H | 3-ethyl-5-isoxazolyl | H |
| 64 | 4-chlorophenyl | H | 3-ethyl-5-isoxazolyl | H |
| 65 | 3-methyl-5-isothiazolyl | H | 3-isopropyl-5-isoxazolyl | H |
| 66 | 5-methyl-3-isoxazolyl | H | 3-isopropyl-5-isoxazolyl | H |
| 67 | 4-pyridyl | H | 3-isopropyl-5-isoxazolyl | H |
| 68 | 4-methyl-1,3-thiazol-2-yl | H | 3-isopropyl-5-isoxazolyl | H |
| 69 | 4-bromophenyl | H | 3-isopropyl-5-isoxazolyl | H |
| 70 | 3-methyl-5-isothiazolyl | H | 3-phenyl-5-isoxazolyl | H |
| 71 | 4-pyridyl | H | 3-phenyl-5-isoxazolyl | H |
| 72 | 4-methyl-1,3-thiazol-2-yl | H | 3-phenyl-5-isoxazolyl | H |
| 73 | 4-bromophenyl | H | 3-phenyl-5-isoxazolyl | H |

TABLE 1-continued

Compounds

| Compound | R¹ | R² | R³ | R⁴ |
|---|---|---|---|---|
| 74 | 3-(4-chlorophenyl)-5-isoxazolyl | H | 3-phenyl-5-isoxazolyl | H |
| 75 | 4-methyl-1,3-thiazol-2-yl | H | 4-thiazolyl | H |
| 76 | 4-pyridyl | H | 4-thiazolyl | H |
| 77 | 6-quinolyl | H | 4-thiazolyl | H |
| 78 | 4-bromophenyl | H | 1-methyl-1H-5-imidazolyl | H |
| 79 | 4-chlorophenyl | H | 1-methyl-1H-5-imidazolyl | H |
| 80 | 5-methyl-3-isoxazolyl | H | 1-methyl-1H-5-imidazolyl | H |
| 81 | 3-methyl-5-isothiazolyl | H | 4-pyridyl | H |
| 82 | 4-methyl-1,3-thiazol-2-yl | H | 4-pyridyl | H |
| 83 | 5-methyl-3-isoxazolyl | H | 4-pyridyl | H |
| 84 | 3-(tert-butyl)-5-isoxazolyl | H | 4-pyridyl | H |
| 85 | 3-methyl-5-isothiazolyl | H | 3-pyridyl | H |
| 86 | 3-methyl-5-isoxazolyl | H | 3-pyridyl | H |
| 87 | 4-methyl-1,3-thiazol-2-yl | H | 3-pyridyl | H |
| 88 | 5-methyl-3-isoxazolyl | H | 3-pyridyl | H |
| 89 | 5-(tert-butyl)-3-isoxazolyl | H | 3-pyridyl | H |
| 90 | 5-methyl-3-isoxazolyl | H | 4-methoxyphenyl | H |
| 91 | 5-methyl-3-isoxazolyl | H | 3,4-difluorophenyl | H |
| 92 | 5-methyl-3-isoxazolyl | H | phenyl | H |
| 93 | 5-methyl-3-isoxazolyl | H | 2-naphthyl | H |
| 94 | 5-methyl-3-isoxazolyl | H | 3-phenoxypropyl | H |
| 95 | 5-methyl-3-isoxazolyl | H | 2-fluorophenyl | H |
| 96 | 5-methyl-3-isoxazolyl | H | 3-methyl-2-butenyl | H |
| 97 | 5-methyl-3-isoxazolyl | H | isopropenyl | H |
| 98 | 5-methyl-3-isoxazolyl | H | 2-methyl-1-propenyl | H |
| 99 | 5-[(4-nitrophenyl) sulfonyl]-1,3-thiazol-2-yl | H | dimethyl | H |
| 100 | 3-methyl-5-isothiazolyl | H | 4-cyanophenyl | 5-methoxy |
| 101 | 5-methyl-3-isoxazolyl | H | 3,4,5-trimethoxybenzyl | 5-cyano |
| 102 | 3-methyl-5-isothiazolyl | H | 4-cyanophenyl | 5-nitro |

The compounds of this invention can be prepared via standard organic synthetic methods, including the methods illustrated in the schemes and the examples herein. Advantageously, the starting materials for these methods are readily available.

Nucleophilic agents are known in the art and are described in the chemical texts and treatises referred to herein, and include reagents having electrons to share. Leaving groups are known in the art and are any stable species that can be detached from a molecule during a reaction (e.g., halides, triflates, alkoxides, or alcohols). A base is known in the art and is any species that has a pair of electrons available to share with a proton (e.g., primary and secondary amines, tert-butoxides, pyridine, or hydrides). The chemicals used in the aforementioned methods can include, for example, solvents, reagents, catalysts, protecting group and deprotecting group reagents and the like. The methods described above can also additionally include steps, either before or after the steps described specifically herein, to add or remove suitable protecting groups in order to ultimately allow synthesis of the compound of the formulae described herein.

As can be appreciated by the skilled artisan, the synthetic schemes herein are not intended to constitute a comprehensive list of all means by which the compounds described and claimed in this application can be synthesized. Further methods will be evident to those of ordinary skill in the art. Additionally, the various synthetic steps described above can be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2nd. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); and subsequent editions thereof.

In general, the indole derivatives of the present invention are prepared according to the synthetic scheme shown below.

Variables and groups in the chemical structural formulae in the methods below are defined as delineated herein for any of the formulae, including formula 1.

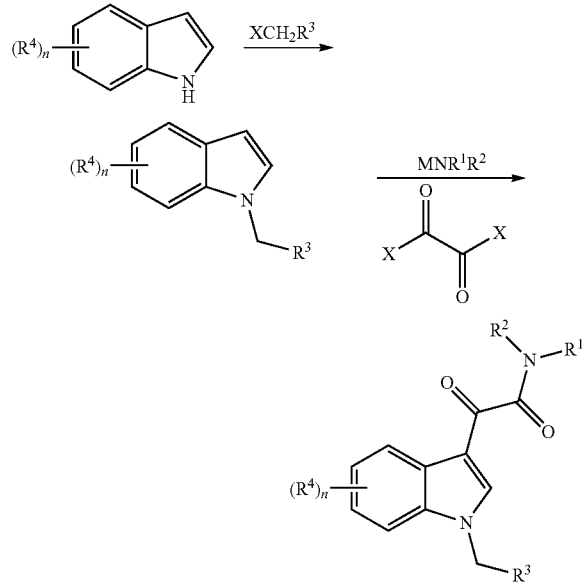

A solution of indolyl compound starting material in a solvent (e.g., tetrahydrofuran, isopropanol, dichloromethane, dioxane, dimethyl formamide, dimethyl sulfoxide, or toluene) is reacted with a base (e.g., sodium hydride, potassium hydroxide, or potassium tert-butoxide) and a compound of the formula $XCH_2R^3$ (where X is a leaving group). The resulting intermediate is reacted with an oxalyl derivative and an amine of the formula $MNR^1R^2$ (where M is H or metal cation, e.g., K, Li, Na), to give compounds of the formulae delineated herein. The desired compounds or intermediates can be isolated and purified using standard techniques or can be reacted further (i.e., "one-pot synthesis") without isolation or purification.

Alternatively, the indolyl compounds of the present invention are prepared according to the following synthetic scheme.

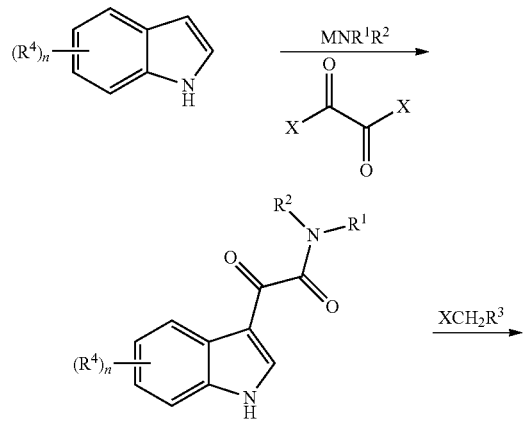

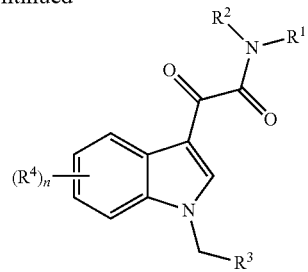

The indolyl starting material is dissolved in a solvent (e.g., diethyl ether, tetrahydrofuran, or dichloromethane) and reacted with an oxalyl derivative (e.g., oxalyl chloride) and an amine of the formula $MNR^1R^2$ (where M is H or metal cation, e.g., K, Li, Na). The intermediate compound is reacted with a compound of the formula $XCH_2R^3$ (where X is a leaving group) to give compounds of the formulae herein. The desired compounds or intermediates can be isolated (and optionally purified) or can be reacted further (i.e., "one-pot synthesis" without isolation or purification).

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention can be modified by appending appropriate functionalities to enhance selective biological properties. Such modifications are known in the art and include those which increase biological penetration into a given biological compartment (e.g., blood, lymphatic system, central nervous system), increase oral bioavailability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, butyrate, citrate, camphorate, camphorsulfonate, ethanesulfonate, formate, fumarate, glycolate, heptanoate, hexanoate, hydrochloride, hydrobromide, 2-hydroxyethanesulfonate, lactate, maleate, malonate, methanesulfonate, 2-naphthalenesulfonate, nicotinate, nitrate, palmoate, pectinate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products can be obtained by such quaternization.

The anticancer, antitumor, cytotoxicity, antiangiogenic or other biological activity of the compounds can be assayed by standard methods and assays known in the art, including those exemplified by the examples described herein. These analyses are useful for assessing and demonstrating the efficacy of the compounds herein as anticancer, antitumor, or cytotoxic agents.

The heterocyclic compounds of the formulae delineated herein can be administered to a patient, for example, in order to treat cancer or to prevent unwanted angiogenesis. The heterocyclic compounds can, for example, be administered in a pharmaceutically acceptable carrier such as physiological saline, in combination with other drugs, and/or together with appropriate excipients.

As the skilled artisan will appreciate, lower or higher doses than those recited above can be required. Specific dosage and treatment regimens for any particular patient will depend upon a variety of factors, including the activity of the specific compound employed, the age, body weight, general health status, sex, diet, time of administration, route of administration, frequency of administration, rate of excretion, drug combination, the severity and course of the disease, condition or symptoms, the patient's disposition to the disease, condition or symptoms, and the judgment of the treating physician.

In the methods of treating, preventing, or relieving symptoms of diseases (e.g., cancer, tumors, proliferation of new blood vessels) in a mammal including any of the pharmaceutical compositions and combinations described above, preferably the mammal is a human. If the pharmaceutical composition includes only the compound of this invention as the active component, such methods can additionally include administering to said mammal an additional therapeutic agent such as, for example, paclitaxel, docitaxel, doxorubicin, daunorubicin, epirubicin, fluorouracil, melphalan, cis-platin, carboplatin, cyclophosphamide, mitomycin, methotrexate, mitoxantrone, vinblastine, vincristine, ifosfamide, teniposide, etoposide, bleomycin, leucovorin, cytarabine, dactinomycin, interferon alpha, streptozocin, prednisolone, procarbazine, SU5416, SU6668, endostatin, angiostatin, combretastatin A4-phosphate, thalidomide, 2-methoxyestradiol, CAI, CC-5013, LY317615. Other suitable agents are delineated in texts and publications, including for example Cancer: Principles & Practice of Oncology, 6th Edition by Vincent T. DeVita, Jr., Samuel Hellman, and Steven A. Rosenberg, Lippincott-Raven Publishers, Philadelphia, USA, 2001. Such additional agent(s) can be administered to the mammal prior to, concurrently with, or following the administration of the composition having a compound of any of the formulae herein.

Pharmaceutical compositions of this invention include a compound of the formulae described herein or a pharmaceutically acceptable salt thereof, an additional agent, such as an anticancer agent, an anti-angiogenic agent (e.g., protamine, heparin, interferons, steroids, DS 4152, AGM 12470, SU5416, SU6668, combretastatin A4-phosphate, angiostatin, endostatin, TNP-470, 2-methoxyestradiol, thalidomide, CAI, CC-5013, LY317615.), and any pharmaceutically acceptable carrier, adjuvant or vehicle. Alternate compositions of this invention include a compound of the formulae described herein or a pharmaceutically acceptable salt thereof, and a pharmaceutically acceptable carrier, adjuvant or vehicle. Such compositions can optionally include additional therapeutic agents, including, for example an additional agent selected from an anticancer agent, an anti-angiogenic agent, an antiviral agent, an antibiotic, a pain relief agent, an anti-anemia agent (e.g., erythropoietin), a cytokine (e.g., granulocyte-macrophage colony-stimulating factor, granulocyte colony-stimulating factor, interleukins) or an antinausea agent. The compositions delineated herein include the compounds of the formulae delineated herein, as well as additional therapeutic agents if present, in amounts effective for achieving a modulation of the levels or the presence of cancerous cells.

The term "pharmaceutically acceptable carrier or adjuvant" refers to a carrier or adjuvant that can be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds of the formulae described herein.

The pharmaceutical compositions of this invention can be administered orally, parenterally, by inhalation spray, topically, rectally, nasally, buccally, vaginally, subdermally, transmucosally, or via an implanted reservoir, preferably by oral administration or administration by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional, intraperitoneally, and intracranial injection or infusion techniques.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

The pharmaceutical compositions of this invention can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient can be suspended or dissolved in an oily phase combined with emulsifying and/or suspending agents. If desired, certain sweetening and/or flavoring and/or coloring agents can be added.

The pharmaceutical compositions of this invention can also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, bees wax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention can also be topically applied to the lower intestinal tract by rectal suppository formulation or in a suitable enema formulation. Topically applied transdermal patches are also included in this invention.

The pharmaceutical compositions of this invention can be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.001 and about 100 mg/kg body weight per day, alternatively between about 0.5 and about 75 mg/kg body weight per day of the anticancer compounds described herein are useful in a monotherapy and/or in combination therapy for the prevention and treatment of cancer. Typically, the pharmaceutical compositions of this invention will be administered from about 1 to about 6 times per day (e.g., at 10 mg-1000 mg/dose) or alternatively, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

When the compositions of this invention include a combination of a compound of the formulae described herein and one or more additional therapeutic or prophylactic agents, both the compound and the additional agent should be present at dosage levels of between about 10 to 100%, and more preferably between about 10 to 80% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

The compounds of this invention can contain one or more asymmetric centers and thus occur as racemates and racemic mixtures, single enantiomers, individual diastereomers and diastereomeric mixtures. All such isomeric forms of these compounds are expressly included in the present invention. The compounds of this invention can also be represented in multiple tautomeric forms (see illustration), in such instances, the invention expressly includes all tautomeric forms of the compounds described herein. All such isomeric forms of such compounds are expressly included in the present invention (e.g., alkylation of a ring system can result in alkylation at multiple sites, the invention expressly includes all such reaction products). All crystal forms of the compounds described herein are expressly included in the present invention.

Substituents on ring moieties (e.g., phenyl, thienyl, etc.) can be attached to specific atoms, whereby they are intended to be fixed to that atom, or they can be drawn unattached to a specific atom (see below), whereby they are intended to be attached at any available atom that is not already substituted by an atom other than H (hydrogen). For example, a structure drawn as:

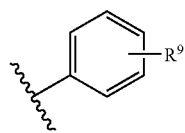

is intended to encompass all of (but is not limited to) the following structures:

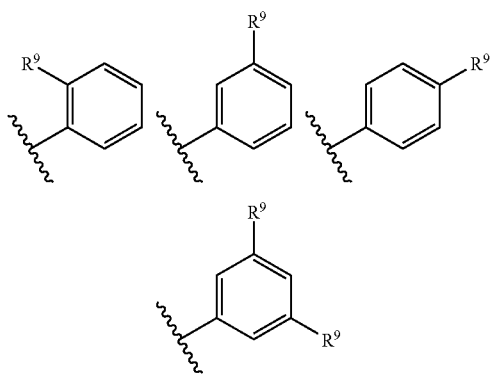

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following example. It should be understood that these examples are for illustrative purposes only and are not to be construed as limiting this invention in any manner.

EXAMPLES

Example 1a

Synthesis of Compound 1

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then α-bromo-p-tolunitrile (1.96 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 6:1 (vol/vol). Yield: 1.97 g, 85%.

A solution of 4-(1H-1-indolylmethyl)benzonitrile (232 mg, 1.0 mmol) in 10 mL diethyl ether was added oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then 4-aminopyridine (94 mg, 1.0 mmol) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran; the organic phase was dried using anhydrous magnesium sulfate and filtered; and the filtrate was concentrated in vacuum. The residue was crystallized from methanol. Yield: 0.21 g, 56%.

NMR: 9.51 (s, 1H), 9.12 (s, 1H), 8.61-8.59 (m, 2H), 8.48 (d, J=6.0 Hz, 2H), 7.66-7.63 (m, 4H), 7.44-7.23 (m, 5H), 5.50 (s, 2H). MS (M+1): 381.

Example 1b

Synthesis of Compound 1

A solution of indole (1.17 g, 10 mmol) in 10 mL diethyl ether was added to oxalyl chloride (2.54 g, 20 mmol) dropwise at 0° C. The reaction mixture was stirred at 0° C. for 3 hours and then the reaction solvent was evaporated. The residue was dissolved in 5 mL tetrahydrofuran and then the 4-aminopyridine (94 mg, 1.0 mmol) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran. The organic phase was dried using anhydrous magnesium sulfate and filtered, and the filtrate was concentrated in vacuum. The residue was crystallized from methanol. Yield: 1.04 g, 63%.

A solution of N1-(4-pyridyl)-2-(1H-3-indolyl)-2-oxoacetamide (825 mg, 5 mmol) in 10 mL tetrahydrofuran was added dropwise to a suspension of potassium tert-butoxide (0.67 g, 6 mmol) in 10 mL tetrahydrofuran. The reaction mixture was stirred at room temperature for 2 hours, then α-bromo tolunitrile (0.98 g, 5 mmol) in 5 mL tetrahydrofuran was added dropwise. The solution was allowed to stand for 4 hours and then 10 mL saturated ammonium chloride was added with stirring. The mixture was extracted three times with a total of 60 mL of tetrahydrofuran and the organic phase was dried using anhydrous magnesium sulfate and filtered. The filtrate was concentrated in vacuum and purified by crystallization from methanol. Yield: 0.99 g, 52%.

NMR: 9.51 (s, 1H), 9.12 (s, 1H), 8.61-8.59 (m, 2H), 8.48 (d, J=6.0 Hz, 2H), 7.66-7.63 (m, 4H), 7.44-7.23 (m, 5H), 5.50 (s, 1H). MS (M+1): 381.

Example 2

Synthesis of Compound 25

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then α-bromo-p-tolunitrile (1.96 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent was used a mixture of n-hexane and ethyl acetate in the ratio 6:1 (vol/vol). Yield: 1.97 g, 85%.

A solution of 4-(1H-1-indolylmethyl)benzonitrile (232 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 2-amino-4-methylisothiazol hydrochloride (151 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was recrystallized from methanol. Yield: 0.19 g, 48%.

NMR: 10.32 (s, 1H), 9.17 (s, 1H), 8.47 (d, J=7.5 Hz, 1H), 7.65-7.22 (m, 7H), 6.82 (s, 1H), 5.49 (s, 2H), 2.47 (s, 3H). MS (M+1): 401.2.

Example 3

Synthesis of Compound 42

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 2-(bromomethyl)furan (1.10 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.42 g, 85%.

A solution of 1-(2-furylmethyl)-1H-indole (197 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 6-aminoquinoline (144 mg, 1.0 mmol) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.29 g, 74%.

NMR: 9.56 (s, 1H), 9.10 (s, 1H), 8.81 (d, J=3.9 Hz, 1H), 8.45-8.40 (m, 2H), 8.12 (d, J=8.7 Hz, 1H), 8.06 (d, J=8.7 Hz, 1H), 7.73 (dd, J=9.0 Hz, J=2.4 Hz, 1H), 7.48-7.31 (m, 4H), 7.19 (s, 1H), 6.35-6.29 (m, 2H), 5.30 (s, 2H). MS (M+1): 396.1

Example 4

Synthesis of Compound 46

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 3-(chloromethyl)thiophene (1.33 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent was used a mixture of n-hexane and ethyl acetate in the ratio 8:1 (vol/vol). Yield: 1.64 g, 77%.

A solution of 1-(3-thienylmethyl)-1H-indole (213 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 3-methyl-5-isoxazolamine (98 mg, 1.0 mmol) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.24 g, 65%.

NMR: 10.07 (s, 1H), 9.00 (s, 1H), 8.47-8.43 (m, 1H), 7.43-7.31 (m, 4H), 7.15 (dd, J=2.9 Hz, J=1.2 Hz, 1H), 6.97 (dd, J=5.0 Hz, J=1.2 Hz, 1H), 6.35 (s, 1H), 5.41 (s, 2H), 2.32 (s, 3H). MS (M+1): 366.

Example 5

Synthesis of Compound 56

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 5-(chloromethyl)-3-methylisoxazole (1.32 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.61 g, 76%.

A solution of 5-(1H-1-indolylmethyl)-3-methylisoxazole (212 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 3-methyl-5-isothiazolamine (114 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.27 g, 71%.

NMR: 10.33 (s, 1H), 9.15 (s, 1H), 8.44 (d, J=6.3 Hz, 1H), 7.45-7.38 (m, 3H), 6.82 (s, 1H), 5.96 (s, 1H), 5.48 (s, 2H), 2.49 (s, 3H), 2.52 (s, 3H). MS (M+1): 381.1.

Example 6

Synthesis of Compound 75

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 4-(chloromethyl)-1,3-thiazole (1.34 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.43 g, 67%.

A solution of 4-(1H-1-indolylmethyl)-1,3-thiazole (214 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 4-methyl-1,3-thiazol-2-amine (114 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.17 g, 45%.

NMR: 9.19 (s, 1H), 8.55 (d, J=2.1 Hz, 1H), 8.49-8.46 (m, 1H), 7.46-7.31 (m, 4H), 7.06 (s, 1H), 6.65 (s, 1H), 5.60 (s, 2H), 2.41 (s, 3H). MS (M+1): 383.1.

Example 7

Synthesis of Compound 78

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 5-(chloromethyl)-1-methyl-1H-imidazole (1.31 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.56 g, 74%.

A solution of 1-[(1-methyl-1H-5-imidazolyl)methyl]-1H-indole (211 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 4-bromoaniline (172 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.22 g, 51%.

NMR: 10.91 (br, 1H), 9.05 (s, 1H), 8.35-8.32 (m, 1H), 7.86-7.83 (m, 2H), 7.70-7.67 (m, 2H), 7.59-7.55 (m, 3H), 7.39-7.35 (m, 2H), 6.04 (s, 2H), 3.85 (s, 3H). MS (M+1): 437.0.

Example 8

Synthesis of Compound 81

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 4-(chloromethyl)pyridine (1.27 g, 10 mmol) in 5 mL tetrahydrofuran was added dropwise. The solution was allowed to stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.35 g, 65%.

A solution of 1-(4-pyridylmethyl)-1H-indole (208 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 3-methyl-5-isothiazolamine (114 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.17 g, 46%.

NMR: 10.34 (s, 1H), 9.18 (s, 1H), 8.60 (d, J=6.0 Hz, 2H), 8.48 (d, J=7.8 Hz, 1H), 7.45-7.22 (m, 3H), 7.08 (d, J=6.0 Hz, 2H), 6.82 (s, 1H), 5.47 (s, 2H), 2.47 (s, 3H). MS (M+1): 377.

Example 9

Each of the indol-3-yl oxoacetamido compounds 1 to 102 in Table 1, was prepared in accordance with methods described above. $^1$H Nuclear magnetic resonance and mass spectroscopy data for each compound was consistent with that for the desired product.

Example 10

In Vitro Cytotoxicity Study

A panel of human cancer cells, gastric NUGC3 and HR, nasopharyngeal HONE1, hepatocellular HEP G2 and HA-22T, colorectal DLD1, lung A549, prostate PC3, breast MCF7 and its adriamycin-resistant MCF7/ADR subline, uterus MES-SA and its adriamycin-resistant MES-SA/Dx5 subline, was purchased from Food Industry Research and Development Institute, Hsinchu, Taiwan R.O.C. or American Type Culture Collection, Manassas, Va. U.S.A. The human cells were seeded at a cell density of 3000 or 4500 cells/100 µl/well in 96-well flat-bottom plates and incubated for 24 hours at 37° C. in a 5% $CO_2$ incubator. A testing compound was dissolved in dimethyl sulfoxide (DMSO) and further diluted into the culture medium for treatments of human cancer cells in vitro. The drug-containing media had a final DMSO concentration of ≦0.3%. The compounds of this invention were prepared in culture media for testing at a range of concentrations from 10, 1, 0.1, 0.01 to 0.001 µM. Each compound solution was (200 µl/well in duplicate) in the cell plates and was treated for 72 hours at 37° C., 5% $CO_2$ in an incubator. Actinomycin D at 5 µM and 0.3% DMSO were used as the positive and vehicle controls, respectively. A calorimetric assay using 3-(4,5-dimethylthiazol-2-yl)-5-(3-carboxymethoxyphenyl)-2-(4-sulfophenyl)-2H-tetrazolium (MTS) and phenazine methosulfate (PMS) was used to determine the potency of the compounds. This assay measured cell viability based on the cellular activity in conversion of a tetrazolium salt into a colored soluble formazan product. The optical density (OD) values were measured at 490 nm with a 1420 multilabel counter VICTOR® from Wallac, Turku, Finland. All of the measured values were subtracted with that of the blank control wells without cells before further calculations. The efficacy data were expressed as a percentage normalized to the vehicle controls as calculated in the following formulae. Inhibitory potency (% of vehicle control)= $[(OD490_{compound} - OD490_{blank})/(OD490_{vehicle} - OD490_{blank})] \times 100\%$. The concentration ($IC_{50}$) of a test compound that inhibits 50% of the cellular activity was determined.

Results

The compounds of this invention were evaluated for cytotoxic activities against a panel of 12 human cancer cells. The concentrations ($IC_{50}$) of 50% inhibition of 20 representative compounds of the invention are shown in Tables 1a and 1b. The compounds exhibited a broad spectrum of anticancer activities among human cancer cell lines. Selectivity of the compounds against different human cancer cells was observed. Likewise, a variety of compounds with diverse chemical structures also exhibited differential activities for a certain cancer cell type. Compound 56 showed potent activities against the nasopharyngeal HONE1 cancer cell at an $IC_{50}$ of 3 to 4 nM, while the compound was less effective up to 60-~100-fold in other cell types.

The possibility of cross-resistance with a typical multidrug resistant compound, adriamycin, was also studied. Certain compounds showed less efficacy in the MCF7/ADR than in MCF7. Certain compounds showed essentially equal efficacy in the parent, breast MCF7 and uterus MES-SA, cancer cells as well as the adriamycin-resistant sublines implicating no cross-resistance with multi-drug resistant compounds and thus potential clinical benefits.

TABLES 1a

Anticancer activity of 20 compounds against a panel of human cancer cell lines.*

| Compounds | DLD1 | HA-22T | HEP G2 | HONE1 | HR | NUGC3 |
|---|---|---|---|---|---|---|
| 3 | 665 | 510 | 383 | 174 | 266 | 279 |
| 25 | 543 | 692 | 1792 | 207 | 340 | 514 |
| 32 | 5650 | 1911 | 4771 | 928 | 2250 | 4850 |
| 24 | 5798 | 2838 | 3594 | 401 | 5456 | 1715 |
| 45 | 593 | 2402 | 1689 | 48 | 316 | 465 |
| 43 | 534 | 200 | 713 | 31 | 291 | 134 |
| 56 | 41 | 123 | 93 | 4 | 8 | 12 |
| 30 | 926 | 558 | 953 | 332 | 739 | 639 |
| 38 | 3720 | 2243 | 3455 | 487 | 2984 | 2006 |
| 65 | 609 | 302 | 720 | 50 | 324 | 242 |
| 59 | 658 | 115 | 613 | 34 | 294 | 262 |
| 42 | 799 | 345 | 3981 | 296 | 453 | 634 |
| 40 | 981 | 1255 | 7720 | 56 | 295 | 395 |
| 77 | 1501 | 469 | >10000 | 380 | 721 | 458 |
| 62 | 651 | 148 | 6813 | 42 | 300 | 137 |
| 63 | 705 | 559 | 2473 | 35 | 78 | 118 |
| 48 | 1429 | 303 | 4133 | 217 | 552 | 206 |
| 50 | 734 | 46 | 1318 | 38 | 128 | 37 |
| 13 | 846 | 356 | 6310 | 98 | 396 | 431 |
| 54 | 397 | 382 | >10000 | 17 | 64 | 27 |

TABLE 1b

Anticancer activity of 20 compounds against a panel of human cancer cell lines.*

| Compounds | A549 | PC3 | MCF7 | MCF7/ADR | MES-SA | MES-SA/Dx5 |
|---|---|---|---|---|---|---|
| 3 | 6397 | 9630 | 640 | 665 | 4709 | 6087 |
| 25 | 545 | 689 | 469 | 5241 | 373 | 398 |
| 32 | ND | ND | 5179 | 5291 | ND** | ND |
| 24 | ND | ND | 7651 | 2553 | ND | ND |
| 45 | 611 | 824 | 611 | 2348 | 306 | 406 |
| 43 | ND | ND | 856 | 412 | ND | ND |
| 56 | 557 | 628 | 36 | 5004 | 293 | 368 |
| 30 | ND | ND | 920 | 847 | ND | ND |
| 38 | ND | ND | 4259 | 4075 | ND | ND |
| 65 | ND | ND | 700 | 710 | ND | ND |
| 59 | ND | ND | 678 | 300 | ND | ND |
| 42 | ND | ND | 928 | 527 | ND | ND |
| 40 | 746 | 398 | 1157 | 1173 | 235 | 263 |
| 77 | ND | ND | 1318 | 595 | ND | ND |
| 62 | ND | ND | 872 | 509 | ND | ND |
| 63 | 1000 | 636 | 747 | 5073 | 312 | 330 |
| 48 | ND | ND | 915 | 371 | ND | ND |
| 50 | ND | ND | 171 | 406 | ND | ND |
| 13 | ND | ND | 577 | 597 | ND | ND |
| 54 | 1668 | 725 | 5025 | 5410 | 268 | 333 |

*MTS assays were carried out and the data were the concentrations ($IC_{50}$) to inhibit 50% of the cancer cell growth expressed in nM.
**ND, not determined Example 11

Evaluation of In Vivo Anticancer Activity

Figure 2:
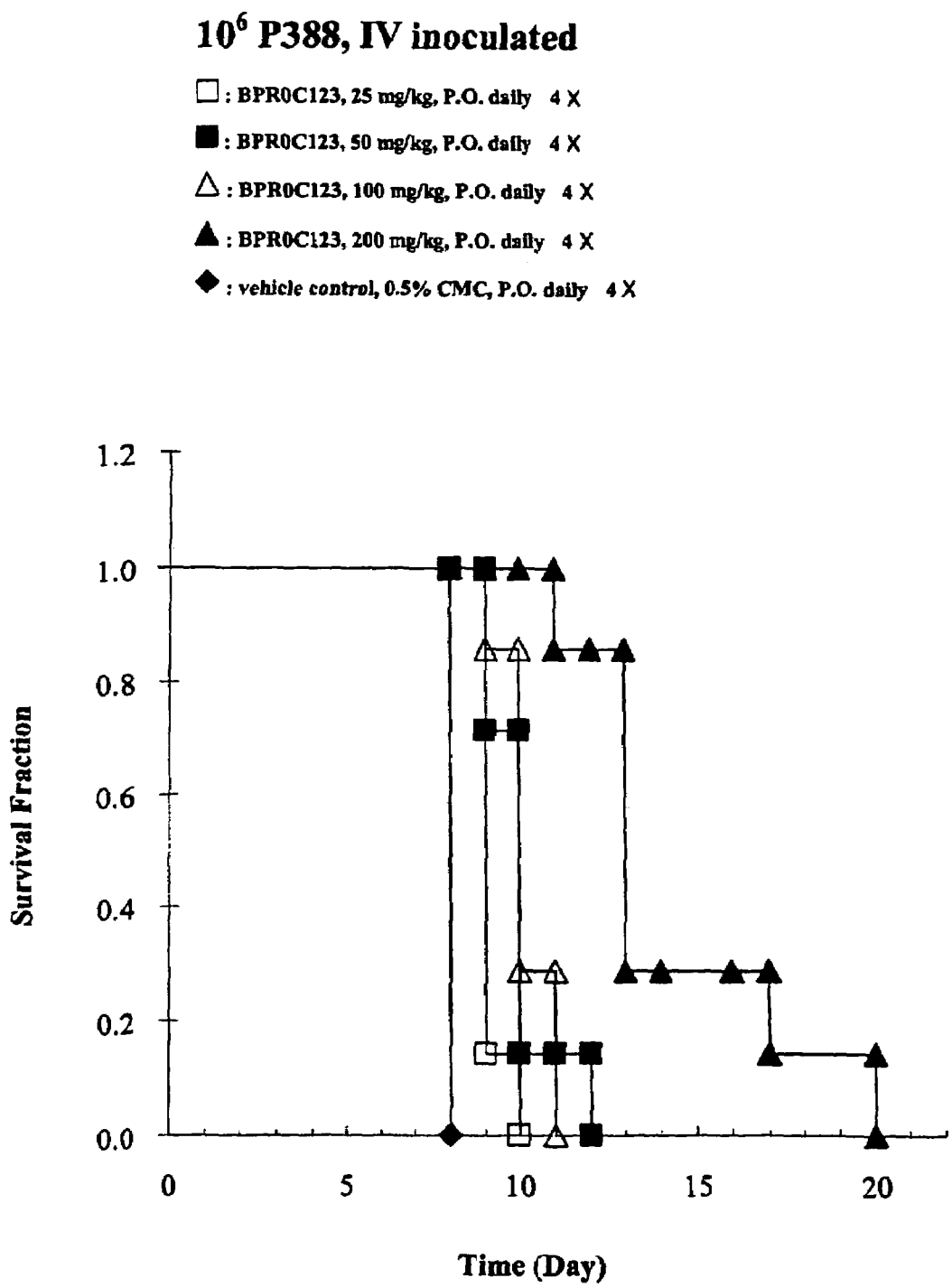
FIG. 2 is a graph of the dose-response relationship of compound 25, showing survival fractions of mice.

The in vivo anticancer activities of the compounds were evaluated by the following murine leukemic P388 model. Inbred female DBA/2 J mice of 4-5 week-old were purchased from the Charles River Laboratories Inc., Wilmington, Mass., USA and the National Laboratory Animals Breeding and Research Center, Taipei, Taiwan, ROC. Murine leukemic P388 cells were purchased from the Japanese Collection of Research Bioresources, Japan. P388 cells were cultured and propagated in RPMI1640 medium supplemented with 50 μM 2-mercaptoethanol and 10% fetal bovine serum. Mice at the age of 6 weeks were grouped as the treatment, negative control and positive control groups at 7 or 8 mice per group. All mice were intravenously inoculated with the P388 cells at one million per mouse one day before the treatments initiated. Compounds of this invention were dissolved in dimethyl sulfoxide (DMSO) and then diluted in 0.5% carboxymethyl cellulose with the final concentration of DMSO less than 0.5%. Different treatment groups were orally given (P.O.), respectively, with compounds of different doses for a pharmacological dose-response relationship. Mice of the negative control group were treated with the dosing vehicle, 0.5% carboxymethyl cellulose. Doxorubicin of the maximal tolerated dose, 10 mg/kg, was given intravenously as an experimental positive control. The cancer cell-inoculated animals were monitored twice daily. Survival fractions of the mice were recorded. FIGS. 1 and 2 show two typical survival curves. The time on which 50% of the P388-inoculated mice was still surviving was defined as the medium survival time and was used to calculate the percentage (normalized to the medium survival time of the control group) of increased in life span after treatment, which was then served as the index of treatment response.

Results and Discussion

Mice of the negative, vehicle control group consistently survived for 7 to 8 days after a single inoculation of one million P388 leukemic cancer cells. The experimental positive control, doxorubicin, also showed a consistent activity of prolongation of survival time in P388-inoculated DBA/2 J mice. The increased life span by the doxorubicin treatment at its maximal tolerated dose was 119±18%, mean±sd.

Compounds 25, 56 and 48 exhibited a dose-dependent activity in the increase of life span. The dose-response relationships of the compounds against the leukemic cancer are summarized in Table 2. It was also noted that the continuation of daily oral treatment with these compounds showed a significant longer survival of the mice. No significant toxicity evident in the body weight loss was observed for the repeatedly dosing regimens through the oral route. The P388 leukemic cancer model results demonstrated the in vivo anticancer activity of the compounds after oral administration.

TABLE 2

| compound | 25 | 56 | 48 |
|---|---|---|---|
| 25 mg/kg, P.O.*, daily, 4× | 14 ± 1% | 26 ± 27% | 25% |
| 50 mg/kg, P.O., daily, 4× | 27 ± 3% | 57 ± 20% | 60% |
| 100 mg/kg, P.O., daily, 4× | 20 ± 8% | 63 ± 17% | 25% |
| 150 mg/kg, P.O., daily, 4× | ND** | ND | 68 ± 25% |
| 200 mg/kg, P.O., daily, 4× | 46 ± 24% | 100 ± 21% | 63% |
| 400 mg/kg, P.O., daily, 4× | ND | ND | 229% |

*P.O., oral administration
**ND, not determined

Example 12

Evaluation of Angiogenesis Inhibition

Establishment of Rat Aorta Tube Formation Assay

The procedures were modified from previous reports (Burbridge and West 2001; Bauer et al. 2000; Nicosai and Ottinetti 1990a) and described as follows. Male Sprague-Dawley rats of 6-8 weeks old were purchased from the National Laboratory Animal Breeding and Research Center (Taipei, Taiwan). The animals were anesthetized with urethane (2 g/kg, intraperitoneal) and the thoracic aortas were quickly harvested in a laminar flow hood. The aortas were rinsed with ice-cold normal saline with 10 μg/ml gentamicin and the attached fibroadipose tissues were removed using micro-dissection scissors. The aortas were cross-sectioned into rings of 1 mm in thickness. A mixture of Matrigel®, purchased from BD Biosciences, solution and the EBM-11 medium, purchased from BioWhittaker Inc., (1:1) with 2% FBS, 0.25 mg/ml, amphotericin B and 10 μg/ml gentamicin was prepared and added at 100 μl to each well of a 48-well plate. The mixture was allowed to gel at 37° C. Aorta rings were then placed onto the gelled matrix and embedded in an additional 150 μl per well of the mixture solution and allowed to gel at 37° C. The aorta rings were then covered with 125 μl of the EGM-II medium and incubated overnight in humidified incubator with 5% $CO_2$/95% air at 37° C. After removal of the EGM-II from the established aorta cultures, the compound-containing media were applied at 300 μl per well to the cultures and then incubated in 5% $CO_2$/95% air at 37° C. for 5 days. The cultures were then subjected to the 3-[4,5-dimethylthiazol-2-yl]-2,5 diphenyl-2H-tetrazolium bromide (MTT)or 3-(4,5-dimethylthiazol-2-yl)-5-(3-carbomethoxyphenyl)-2H-tetrazolium (MTS) assay and OD490 nm values measured. The testing compounds were dissolved in dimethyl sulfoxide (DMSO) and prepared in EBM-II media with at a final concentration of DMSO less than 0.1%.

MTT Staining

The capillary-like, tube structure of the outgrown rat aorta endothelial cells was easily visualized by MTT staining. The medium on top of the matrix was removed from the established aorta ring cultures. MTT solution of 5 mg/ml in saline was added to the cultures at 100 μl/well and the cultures were incubated in a $CO_2$ incubator at 37° C. for 24 hr. The stained cultures were then examined under a microscope DMIRB from Leica and photos taken with a digital camera.

MTS Assay

Inhibition activity was also assessed in the following manner. The reductive reaction of MTS initiated by the viable cellular mitochondrial activity was used as a basis for the measurement of cell viability (Cory et al. 1991; Gieni et al. 1995). To the rat aorta ring cultures 300 μl of a solution containing 100 μg MTS and 1 μg, phenazine methosulfate was added per well and incubated in 5% $CO_2$/95% air at 37° C. for 24 hr. During the incubation, MTS was converted to formazan product. At the end of incubation, the solution overlaying the gel was well-mixed and 100 μl aliquots were transferred into a 96-well plate for measurement of OD490 nm with a spectrophotometer VICTOR™-II from Wallac Oy.

The compounds listed in Table 3 were screened for angiogenesis inhibition. The control compound, ASTA, was D-24851, N—[pyridin-4-yl]-[1-(4-chlorobenzyl)-indol-3-yl]-glyoxylic acid amide. Noninhibitors were indicated by the symbol (−), meaning that the extent of endothelial cell growth was essentially at the same level as that of the control. The most potent inhibitors received a score of (+++++), indicating essentially no measurable endothelial cell growth.

TABLE 3

| Compound | Final conc. | Inhibition Score |
|---|---|---|
| ASTA compound | 1 μg/ml | ++++ |
| 3 | 0.3 μg/ml | +++++ |
| 25 | 0.3 μg/ml | +++++ |
| 32 | 0.3 μg/ml | +++++ |
| 24 | 0.3 μg/ml | − |
| 45 | 0.3 μg/ml | +++++ |
| 56 | 0.3 μg/ml | +++++ |
| 38 | 0.3 μg/ml | − |
| 27 | 1 μg/ml | +++ |
| 65 | 0.3 μg/ml | +++++ |
| 12 | 1 μg/ml | +++ |
| 56 | 1 μg/ml | − |
| 59 | 0.3 μg/ml | +++++ |

TABLE 3-continued

| Compound | Final conc. | Inhibition Score |
|---|---|---|
| 42 | 0.3 µg/ml | +++++ |
| 40 | 0.3 µg/ml | +++++ |
| 77 | 0.3 µg/ml | +++++ |
| 62 | 0.3 µg/ml | ++ |
| 63 | 0.3 µg/ml | +++++ |
| 13 | 0.3 µg/ml | +++++ |
| 54 | 0.3 µg/ml | +++++ |
| 44 | 1 µg/ml | +++++ |

Example 13

Evaluation of Antitumor Activity

Human colorectal SW480 cancer cells were subcutaneously implanted into the young male athymic nude mice at 1 million cells per mouse. The treatment schedule of 200 mg/kg daily oral administration for 6 weeks was initiated at the time which the tumor size reaches 50~100 mm³. Compound 56 was orally gavaged to the nude mice subcutaneously bearing human colorectal SW480 tumor xenograft based on the treatment schedule. The tumor size and body weight of the animals were monitored twice a week through out the 70-day period of observation. The tumor growth was suppressed by the daily oral treatments of compound 56. Tumor sizes of the treated and vehicle control groups were compared at the end of 70-day observation. The size of tumor mass subcutaneously implanted in the nude mice for the treated group was reduced to 26% compared to that of the vehicle control group at the end of the observation period. There was no obvious toxicity as noted by no significant loss of the body weight for the oral multiple dosing treatment.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an angiogenesis-mediated disease comprising administering to a subject in need thereof an effective amount of a compound of formula 1:

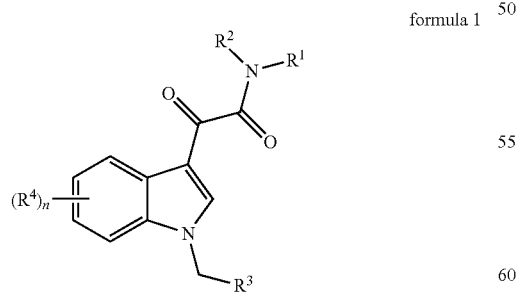

formula 1 wherein, $R^1$ is isoxazolyl, thiazolyl, isothiazolyl, 1,3,4-thiadiazolyl, 1,3-benzothiazolyl, quinolyl, isoquinolyl, thionaphthenyl, or benzofuranyl, each being optionally substituted with 1-6 $R^5$ groups;

$R^2$ is H, C1-C10 alkyl, or aryl, each being optionally substituted with 1-4 $R^5$ groups;

$R^3$ is C1-C10 alkyl, C2-C10 alkenyl, C2-C10 alkynyl, C3-C10 cycloalkyl, C4-C10 cycloalkenyl, aryl, furyl, thiophenyl, isoxazolyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, indolyl, piperazinyl, pyrrolidinyl, dioxanyl, morpholinyl, or tetrahydrofuranyl, each being optionally substituted with 1-4 $R^5$ groups;

each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2OR^7$;

n is 0, 1, 2, 3, or 4;

each $R^5$ is independently H, C1-C10 alkyl optionally substituted with 1-4 $R^6$ groups, C2-C10 alkenyl, C2-C10 alkynyl, C3-C10 cycloalkyl, aryl optionally substituted with 1-4 $R^6$ groups, furyl, thiophenyl, isoxazlyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, or indolyl, each optionally substituted with 1-4 $R^6$ groups, piperazinyl, pyrrolidinyl, dioxanyl, morpholinyl, or tetrahydrofuranyl, each optionally substituted with 1-4 $R^6$ groups, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2O$ $R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$;

each $R^6$ is independently C1-C10 alkyl, C2-C10 alkenyl, C2-C10 alkynyl, halo, haloalkyl, CN, $NO_2$, $OR^7$, or $SO_2R^7$;

each $R^7$ is independently H, C1-C10 alkyl, C2-C10 alkenyl, C2-C10 alkynyl, C3-C10 cycloalkyl, aryl, furyl, thiophenyl, isoxazolyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, indolyl, piperazinyl, pyrrolidinyl, dioxanyl, morpholinyl, or tetrahydrofuranyl, each optionally substituted with 1-4 $R^8$ groups;

each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1-4 independent OH, halo, CN, $NO_2$, or $CO_2H$;

the angiogenesis-mediated disease being proliferative retinopathy, psoriasis, or rheumatoid arthritis.

2. The method of claim 1, wherein $R^1$ is isothiazolyl, isoxazolyl, or thiazolyl, each being optionally substituted with 1-4 C1-C10 alkyl.

3. The method of claim 1, wherein $R^1$ is 3-methyl-5-isothiazolyl.

4. The method of claim 1, wherein each $R^3$ is cyanophenyl, chlorophenyl, 3-methyl-5-isoxazolyl, 3-phenyl-5-isoxazoyl, pyridyl, or thiophenyl.

5. The method of claim 1, wherein $R^1$ is 3-methyl-5-isothiazolyl, 3-methyl-5-isoxazolyl, 3-phenyl-5-isoxazolyl, 3-tert-butyl-5-isoxazolyl, 4-methyl-1,3-thiazol-2-yl, or 1,4-benzodioxan-6-yl, thiazolyl; and $R^3$ is cyanophenyl, 3-methyl-5-isoxazolyl, or thiophenyl.

6. The method of claim 1, wherein the compound is

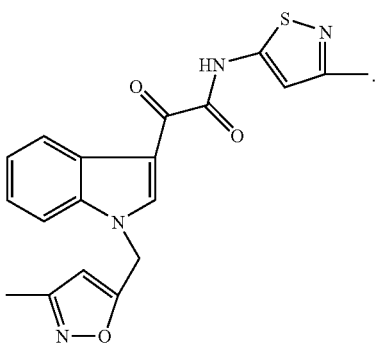

7. A method of treating an angiogenesis-mediated disease comprising administering to a subject in need thereof an effective amount of a compound of the formula 1:

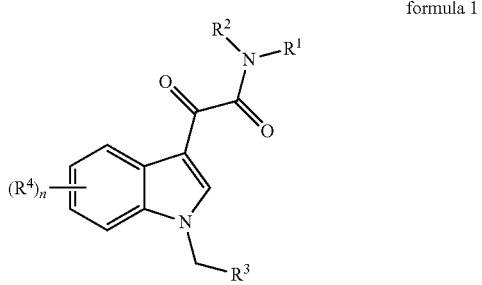

formula 1 wherein,
- $R^1$ is C1-C10 alkyl, C2-C10 alkenyl, C2-C10 alkynyl, C3-C10 cycloakyl, C4-C10cycloalkenyl, aryl, furyl, thiophenyl, isoxazolyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, indolyl, piperazinyl, pyrrolidinyl, dioxanyl, morpholinyl, or tetrahydrofuranyl, each being optionally substituted with 1-6 $R^5$ groups;
- $R^2$ is H, C1-C10 alkyl, or aryl, each being optionally substituted with 1-4 $R^5$ groups;
- $R^3$ is cyanophenyl, furanyl, thiophenyl, isoxazolyl, thiazolyl, imidazolyl, 4,5-dihydro-5-isoxazolyl, or naphthyl; each being optionally substituted with 1-4 $R^5$ groups;
- each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)NR^7R^7$, $NR^7C(O)R^7$, $NR^7(COOR^7)$, $NR^7S(O)_2NR^7R^7$, or $NR^7S(O)_2R^7$, $S(O)_2O R^7$,
- n is 0, 1, 2, 3, or 4;
- each $R^5$ is independently H, C1-C10 alkyl optionally substituted with 1-4 $R^6$ groups, C2-C10 alkenyl, C2-C10 alkynyl, C3-C10 cycloalkyl, aryl optionally substituted with 1-4 $R^6$ groups, furyl, thiophenyl, isoxazolyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, or indolyl, each optionally substituted with 1-4 $R^6$ groups, piperazinyl, pyrrolidinyl, dioxanyl, morpholinyl, or tetrahydrofuranyl, each optionally substituted with 1-4 $R^6$ groups, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2O R^7$, $S(O)_2NR^7R^7$, $NR^7C(O)NR^7R^7$, $NR^7C(O) R^7$, $NR^7(COOR^7)$, $NR^7S(O)_2NR^7R^7$, or $NR^7S(O)_2R^7$;
- each $R^6$ is independently C1-C10 alkyl, C2-C10 alkenyl, C2-C10 alkynyl, C3-C10 cycloalkyl, halo, haloalkyl, CN, $NO_2$, $OR^7$, or $SO_2R^7$;
- each $R^7$ is independently H, C1-C10 alkyl, C2-C10 alkenyl, C2-C10 alkynyl; C3-C10 cycloalkyl; aryl, furyl, thiophenyl, isoxazolyl, thiazolyl, imidazolyl, pyridyl, isothiazolyl, 1,3,4-thiadiazolyl, 1,3-benzothiazolyl, thionaphthenyl, benzofuranyl, benzimidazolyl, pyrimidinyl, quinolinyl, isoquinolyl, indolyl, piperazinyl, pyrrolidinyl, dioxanyl, morpholinyl, or tetrahydrofuranyl, each optionally substituted with 1-4 $R^8$ groups;
- each $R^8$ is independently H, OH, $OR^9$, C1-C10 alkyl, halo, aryl, $NO_2$, or CN; and
- each $R^9$ is independently H, C1-C10 alkyl, or aryl; each being optionally substituted with 1-4 independent OH, halo, CN, $NO_2$, or $CO_2H$;
- the angiogenesis-mediated disease being proliferative retinopathy, psoriasis, or rheumatoid arthritis.

8. The method of claim 7, wherein each $R^3$ is cyanophenyl, furanyl, or thiophenyl.

9. The method of claim 7, wherein each $R^1$ is 3-methyl-5-isothiazolyl, pyridyl, halophenyl, or methoxyphenyl; and $R^3$ is 3-alkyl-5-isoxazolyl, 3-aryl-5-isoxazolyl, or cyanophenyl.

10. The method of claim 7, wherein each $R^1$ is 3-methyl-5-isothiazolyl or 6-quinolyl; and $R^3$ is furanyl, thiophenyl, or 1-methyl-1H-5-imidazolyl.

11. The method of claim 1, wherein the angiogenesis-mediated disease is proliferative retinopathy.

12. The method of claim 1, wherein the angiogenesis-mediated disease is psoriasis or rheumatoid arthritis.

13. The method of claim 7, wherein the angiogenesis-mediated disease is proliferative retinopathy.

14. The method of claim 7, wherein the angiogenesis-mediated disease is psoriasis or rheumatoid arthritis.

* * * * *